(12) United States Patent
Chang

(10) Patent No.: US 8,552,151 B2
(45) Date of Patent: Oct. 8, 2013

(54) MUTANT BLUE FLUORESCENT PROTEIN AND METHOD OF USING THE SAME FOR FLUORESCENCE ENERGY TRANSFER AND BLUE FLUORESCENT FISH

(75) Inventor: Ming-Chung Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/484,893

(22) Filed: May 31, 2012

(65) Prior Publication Data

US 2012/0238726 A1 Sep. 20, 2012

Related U.S. Application Data

(63) Continuation of application No. 12/626,145, filed on Nov. 25, 2009, now abandoned.

(51) Int. Cl.
*C07K 14/00* (2006.01)
*C07H 21/04* (2006.01)
*C12N 1/20* (2006.01)
*C12N 15/00* (2006.01)

(52) U.S. Cl.
USPC ............... 530/350; 435/252.3; 435/320.1; 536/23.2; 536/23.7

(58) Field of Classification Search
USPC .......... 530/350; 435/252.3, 320.1; 536/23.2, 536/23.7
See application file for complete search history.

*Primary Examiner* — Maria Leavitt
(74) *Attorney, Agent, or Firm* — WPAT, P.C.; Anthony King

(57) ABSTRACT

The present invention discloses a mutant blue fluorescent protein (BFP), mutated by an error-prone PCR method or a DNA shuffling method with using a BFPvv D7 of SEQ ID NO:2 as parents, obtained from a wild type blue fluorescent protein BfgV of SEQ ID NO:1, obtained from *Vibrio vulnificus*, wherein a set of mutation positions of the mutant BFP corresponding to SEQ ID NO:2 comprises position 176 and position 178. In a preferred embodiment, the set of mutation positions of the mutant BFP corresponding to SEQ ID NO:2 comprises a S176R mutation or a V178I mutation. Moreover, methods of using the blue fluorescent proteins from *Vibrio vulnificus* for fluorescence resonance energy transfer (FRET) and a blue fluorescent fish are also provided.

6 Claims, 11 Drawing Sheets

SEQUENCE LISTING

```
<160> NUMBER OF SEQ ID NOS: 3

<210> SEQ ID NO 1
<211> LENGTH: 239
<212> TYPE: PRT
<213> ORGANISM: Vibrio vulnificus

<400> SEQUENCE: 1
```

Met Lys Lys Leu Val Val Ile Thr Gly Ala Ser Ser Gly Ile Gly Glu
1               5                   10                  15

Ala Ile Ala Arg Arg Phe Ser Glu Glu Gly His Pro Leu Leu Leu Leu
                20                  25                  30

Ala Arg Arg Val Glu Arg Leu Glu Ala Leu Asn Leu Pro Asn Thr Leu
            35                  40                  45

Cys Ala Gln Val Asp Val Thr Asp Lys Asn Thr Phe Asp Ala Ala Ile
        50                  55                  60

Thr Arg Ala Glu Lys Ile Tyr Gly Pro Ala Asp Val Leu Val Asn Asn
65                  70                  75                  80

Ala Gly Val Met Leu Leu Gly Gln Ile Asp Thr Gln Glu Ala Asn Glu
                85                  90                  95

Trp Gln Arg Met Phe Asp Val Asn Val Leu Gly Leu Leu Asn Gly Met
            100                 105                 110

Gln Ala Val Leu Ala Pro Met Lys Ala Arg Asn Ser Gly Thr Ile Ile
        115                 120                 125

Asn Ile Ser Ser Ile Ala Gly Lys Lys Thr Phe Pro Asp His Ala Ala
    130                 135                 140

Tyr Cys Gly Thr Lys Phe Ala Val His Ala Ile Ser Glu Asn Val Arg
145                 150                 155                 160

Glu Glu Val Ala Ala Ser Asn Val Arg Val Thr Thr Ile Ala Pro Gly
                165                 170                 175

Ala Val Glu Thr Glu Leu Leu Ser His Thr Thr Ser Gln Gln Ile Lys
            180                 185                 190

Asp Gly Tyr Asp Ala Asn Lys Val Asp Met Gly Gly Val Leu Ala Ala
        195                 200                 205

Asp Asp Val Ala Arg Ala Val Leu Phe Ala Tyr Gln Gln Pro Gln Asn
    210                 215                 220

Val Cys Ile Arg Glu Ile Ala Leu Ala Pro Thr Lys Gln Gln Pro

```
225                 230                 235

<210> SEQ ID NO 2
<211> LENGTH: 239
<212> TYPE: PRT
<213> ORGANISM: Artificial Sequence
<220> FEATURE:
<223> OTHER INFORMATION: Variant derived Vibrio vulnificus

<400> SEQUENCE: 2

Met Lys Lys Leu Val Val Ile Thr Gly Ala Ser Ser Gly Ile Gly Gl

-continued

```
                65                    70                    75                    80
        Ala Gly Met Met Leu Leu Gly Gln Ile Asp Thr Gln Glu Ala Asn Glu
                        85                    90                    95

Trp Gln Arg Met Phe Asp Val Asn Val Leu Gly Leu Leu Asn Gly Met
                        100                   105                   110

Gln Ala Val Leu Ala Pro Met Lys Ala Arg Asn Cys Gly Thr Ile Ile
                    115                   120                   125

Asn Ile Ser Ser Ile Ala Gly Lys Lys Thr Phe Pro Asp His Ala Ala
                    130                   135                   140

Tyr Cys Gly Thr Lys Phe Ala Val His Ala Ile Ser Glu Asn Val Arg
        145                 150                   155                   160

Glu Glu Val Ala Ala Ser Asn Val Arg Val Met Thr Ile Ala Pro Arg
                        165                   170                   175

Ala Ile Lys Thr Glu Leu Leu Ser His Thr Thr Ser Gln Gln Ile Lys
                        180                   185                   190

Asp Gly Tyr Asp Ala Asn Lys Val Asp Met Gly Gly Val Leu Ala Ala
                        195                   200                   205

Asp Asp Val Ala Arg Ala Val Leu Phe Ala Tyr Gln Gln Pro Gln Asn
                    210                   215                   220

Val Cys Ile Arg Glu Ile Ala Leu Ala Pro Thr Lys Gln Gln Pro
        225                 230                   235
```

MUTANT BLUE FLUORESCENT PROTEIN AND METHOD OF USING THE SAME FOR FLUORESCENCE ENERGY TRANSFER AND BLUE FLUORESCENT FISH

CROSS-REFERENCE TO RELATED APPLICATION

This application is a continuation of the now Abandoned U.S. application Ser. No. 12/626,145, filed on Nov. 25, 2009, the disclosure of which is incorporated herein in its entirety by reference.

BACKGROUND OF THE INVENTION

1. Field of the Invention

The present invention relates to the field of molecular and cellular biology. More specifically, the present invention relates to a mutant blue fluorescent protein (BFP) capable of existing in an anaerobic or aerobic system and methods of using the same for fluorescence resonance energy transfer (FRET) and a blue fluorescent fish.

2. Description of Related Art

Fluorescent proteins, such as green fluorescent proteins (GFPs) from *Aequorea victoria* or GFP-like fluorescent proteins, have become an invaluable tool in cell biology. Over the last several years, GFP variants with altered fluorescence spectra, improved folding properties, increased brightness and altered pH-sensitivity have been increased (Tsien, 1998; Chudakov et al., 2005), and these GFP variants are widely used in the fields of biochemistry, molecular and cell biology, medical diagnostics and drug screening methodologies.

When GFP family proteins are used as reporter molecules, newly-synthesized GFP family polypeptides need to mature properly before emitting fluorescence. The maturation involves two steps: firstly, the protein folding into a nearly native conformation, and then cyclization of an internal tripeptide followed by oxidation. Therefore, the intrinsic brightness of the GFP family proteins in mammalian cells are determined by their expressions, efficient foldings and maturations at 37° C. An additional factor affecting the brightness of GFP family proteins in living organisms is that they strictly require oxygen as a cofactor for fluorescence formation. In fact, all members of the GFP family lose their luminance under rigorously anoxic conditions (<0.75 µM $O_2$.) (Hansen et al., 2001). However, as described in the previous reports of the present inventors (Chang et al., 2004 (vol. 322); Chang et al., 2004 (vol. 319)), a blue fluorescent protein, BfgV found from *Vibrio vulnificus*, fluoresces through augmenting the intrinsic fluorescence of NADPH bound to it. Since NADPH is a common cofactor in most living organisms whether they are aerobic or anaerobic, BfgV and its improved variant, D7, can theoretically fluoresce in both aerobic living cells and anaerobic living cells (e.g. cancer cells). Consequently, BfgV variants with improved folding properties and increased brightness would be valuable in multicolor fluorescence experiments that allow in vivo labeling and detection in both the presence and absence of oxygen.

One technique for monitoring protein-protein interactions in both in vitro and in vivo assays is based on fluorescence resonance energy transfer (FRET). In this process, energy will transfer from one fluorophore (donor) to another (acceptor) when the donor emission spectrum significantly overlaps the acceptor absorption spectrum by a considerable percentage (30%) and these two fluorophores are closely approximated (within 10 nm). Fluorescent proteins with different emission wavelengths across the visible spectrum provide a variety of suitable donor-acceptor pairs for FRET.

Various methods of FRET measurements have been used to visualize protein-protein interactions. Recently, 3-FRET method that is capable of measuring FRET signals within a system of three donor-acceptor pairs, such as BFP coupled with GFP, cyan fluorescent protein (CFP) coupled with yellow fluorescent protein (YFP) and GFP coupled with red fluorescent protein (RFP), and multiple-FRET imaging by using two independently excitable FRET pairs have been reported. A bright and reasonably photostable fluorescent protein with fluorescence at ~450 nm would be valuable in multicolor fluorescence experiments. Among the fluorescent proteins reported to date, a blue fluorescent protein (BFP) with excitation and emission maxima at 380 and 446 nm, respectively, which was developed from wild-type GFP by substitution of tyrosine 66, is particularly interesting because it is expected to be suitably paired with the most frequently used fluorescent proteins, EGFPs (enhanced GFPs), for multicolor imaging. However, BFP is dimly fluorescent in vitro and in vivo. Although a few enhanced BFPs (EBFPs) have been developed by introducing several mutations into BFPs, EBFPs are rarely used so far because of still having a undesirably low fluorescence quantum yield (QY), thereby being weakly fluorescent, and remaining relatively sensitive to photobleaching (Kremers et al., 2007). Therefore, EBFPs with further improvements in both brightness (i.e. with reasonably high QY) and photostability would be desirable. Recently, an ultramarine fluorescent protein, Sirius, with increased photostability and pH insensitivity has been reported. Since Sirius has an emission peak at 424 nm, it is spectrally compatible for 2-color imaging with EGFP (Tomosugi et al., 2009).

In addition, one major drawback shared by most newly discovered wild-type fluorescent proteins is that they are dimeric. Generally, the proteins exist as homodimers. However, when more than one form of a given fluorescent protein is expressed in a single cell or is mixed in vitro, heterdimers can form if the dimerization interfaces for the different fluorescent proteins are complementary. Heterodimerization is undesirable when fluorescent proteins are used to be expressed as a fusion to another protein of interest or when they are used in FRET. Many of the wild-type fluorescent proteins, however, can be engineered into monomers or tandem dimmers, which can then undergo further optimization.

To date, there have been no reports of BFP mutants still having high fluorescence quantum yield (QY), enhanced fluorescence and slow photobleaching at not only high temperature condition (e.g. 37° C.) but also at an anaerobic environment. Such mutants would provide obvious and significant advantages for use as cell markers or protein expression indicators in prokaryotic and, especially, eukaryotic systems where the stand physiological temperature is 37° C. and some of which are anaerobic (e.g. cancer cells), and for applying for FRET well.

SUMMARY OF THE INVENTION

Accordingly, an objective of the present invention is to provide a novel mutant blue fluorescent protein (BFP) having improved fluorescent properties comprising higher fluorescence quantum yield (QY), stronger fluorescence intensity and not sensitive to photobleaching at not only high temperature condition but at an anaerobic environment.

A mutant BFP provided in accordance with the present invention is mutated by an error-prone PCR method or a DNA shuffling method with using a BFPvv D7 of SEQ ID NO:2 as parents, obtained from a wild type blue fluorescent protein BfgV of SEQ ID NO:1, obtained from *Vibrio vulnificus*, wherein a set of mutation positions of the mutant BFP corresponding to SEQ ID NO:2 comprises position 176 and position 178. In a preferred embodiment, the mutant BFP is mutated by a S176R or V178I substitution in which the mutant BFP is 1.2-4 times the fluorescent intensity of the BFPvv D7 of SEQ ID NO:2 and has fluorescence spectra with an excitation peak at 352 nm, and an emission peak at 440 nm. The mutant BFP of the present invention further exhibits extremely stable fluorescence intensity at an aerobic or anaerobic system and is able to fluoresce at low temperatures, such as 20° C., or at high temperatures, such as 37° C.

In addition, a nucleic acid comprising a sequence encoding the mutant BFP of the present invention is also provided. Optionally, the nucleic acid can be functionally linked to an expression, such as a promoter, and/or integrated into a vector. The nucleic acid encoding the mutant BFP may be used to transform or transfect host cells, such as bacterial, plant or animal cells, and such transformed or transfected cells are also provided according to the present invention.

The present invention also provides a method of using a BFP for fluorescence resonance energy transfer (FRET), comprising using the above-described mutant BFP, the BFPvv D7 of SEQ ID NO:2, or the BfgV of SEQ ID NO:1 as a fluorophore. In a preferred embodiment, the above-described mutant BFP, the BFPvv D7 of SEQ ID NO:2, or the BfgV of SEQ ID NO:1 is used as a donor fluorophore and one of several green fluorescent protein (GFP) variants is used as an acceptor fluorophore.

Moreover, the present invention further provides a method of using a BFP for producing a blue fluorescent fish, comprising using the above-described mutant BFP, the BFPvv D7 of SEQ ID NO:2, or the BfgV of SEQ ID NO:1 as a fluorophore by a transgenic technology.

In brief, a mutant BFP and methods of using the same for FRET and a fluorescent fish in accordance with the present invention provide one or more of the following advantages:

(1) The mutant BFP of the present invention may be useful in a variety of different biological applications, comprising fluorescence-activated cell sorting (FACS) screening methods for studying various vector components, e.g. promoters, repressors; for developing improved methods of monitoring and/or improving gene expression; and for studying the tissue specificity of a particular protein.

(2) The mutant BFP of the present invention has improvements in both brightness and photostability, thereby suitable to apply for FRET, particularly for multiple-FRET imaging with single-wavelength excitation, which is a powerful method for detection of protein-protein interaction, enzyme activities and small molecules in the intracellular milieu, so as to be able to report biochemical phenomena in living cells. Additionally, it is also suitable to apply for producing a blue fluorescent fish.

(3) The mutant BFP of the present invention has a propensity to form a monomer, thereby significantly reducing the surface area contacted with proteins such that the accuracy of detecting the protein of interest can be largely increased.

(4) The mutant BFP of the present invention will not lose its luminance even in anaerobic conditions, not like all GFP-like fluorescent proteins. As different from GFP-like proteins, a NADPH-dependent mutant BFP will illuminate through NADPH as a chromophore; being put in more simple terms, the oxygen-dependent maturation process won't be needed in the mutant BFP of the present invention. In addition, UV-excitation (352 nm) permits the mutant BFP to illuminate visible blue light (440 nm) in vivo without oxygen.

(5) Anaerobic bacteria were reported as a tumor-targeting marker. The expression of the mutant BFP in accordance with the present invention in these tumor-targeting anaerobic bacteria will show the location of tumor, and it will result in a great potential that contributes to cancer research and treatment.

(6) The mutant BFP of the present invention can be applied for a BiFC assay. The basic rationale of BiFC assay is to blend two nonfluorescent fragments from a split mutant BFP of the present invention to two interaction partners. Once done, the two proteins interact with each other, and the interaction should bring the two nonfluorescent fragments into close proximity that offers reconstitution of an intact fluorescent protein molecule. As a result, the fluorescent signal will indicate the interaction of the two proteins of interest.

(7) The mutant BFP of the present invention may be applied for a BiFC-FRET assay. The basic rationale of BiFC-FRET assay is combination of both BiFC and FRET assays to visualize ternary complexes in living cells. In the BiFC-FRET assay, two proteins (A and B) are being blended to two non-fluorescent fragments obtained from fluorescent protein GFP, but the third protein (C) is fused to the full-length mutant BFP of the present invention. The interaction between proteins A and B will then be further recompose an intact GFP, and it will then serves as a FRET acceptor. Should protein C interact with proteins A or B or both, the interaction can bring the mutant BFP (FRET donor) close to the reconstituted GFP and it allows FRET to occur. Hence, BiFC-FRET assay can work to provide evidence of ternary complex formation.

Other aspects of the present invention will be illustrated partially in the subsequent detailed descriptions, conveniently considered partially through the teachings thereof, or comprehended by means of the disclosed embodiments of the present invention. Various aspects of the present invention can be understood and accomplished by using the components and combinations specifically pointed out in the following claims. It is noted that the aforementioned summary and the following detailed descriptions of the present invention are exemplary and illustrative, rather than being used to limit the scope of the present invention thereto.

OTHER PUBLICATIONS

Chang et al, "Bright fluorescence of a novel protein from *Vibrio vulnificus* depends on NADPH and the expression of this protein is regulated by a LysR-type regulatory gene," Biochem. Biophys. Res. Commun., 319: 207-213 (2004).

Chang et al, "Fluorescent intensity of a novel NADPH-binding protein of *Vibrio vulnificus* can be improved by directed evolution," Biochem. Biophys. Res. Commun., 322: 303-309 (2004).

Chudakov et al., "Fluorescent proteins as a toolkit for in vivo imaging," Trends Biotechnol., 23: 605-613 (2005).

Hansen et al., "Assessment of GFP fluorescence in cells of *Streptococcus gordonii* under conditions of low pH and low oxygen concentration," Microbiology, 147: 1383-1391 (2001).

Kremers et al., "Improved green and blue fluorescent proteins for expression in bacteria and mammalian cells," 46: 3775-3783 (2007).

Tomosugi et al., "An ultramarine fluorescent protein with increased photostability and pH insensitivity," 6: 351-353 (2009).

Tsien, "The green fluorescent protein," Annu. Rev. Biochem. 67:509-544 (1998).

BRIEF DESCRIPTION OF THE DRAWINGS

The exemplary embodiments of the present invention will be understood more fully from the detailed description given below and from the accompanying drawings of various embodiments of the invention.

DETAILED DESCRIPTION OF THE PREFERRED EMBODIMENTS

Figure 1:
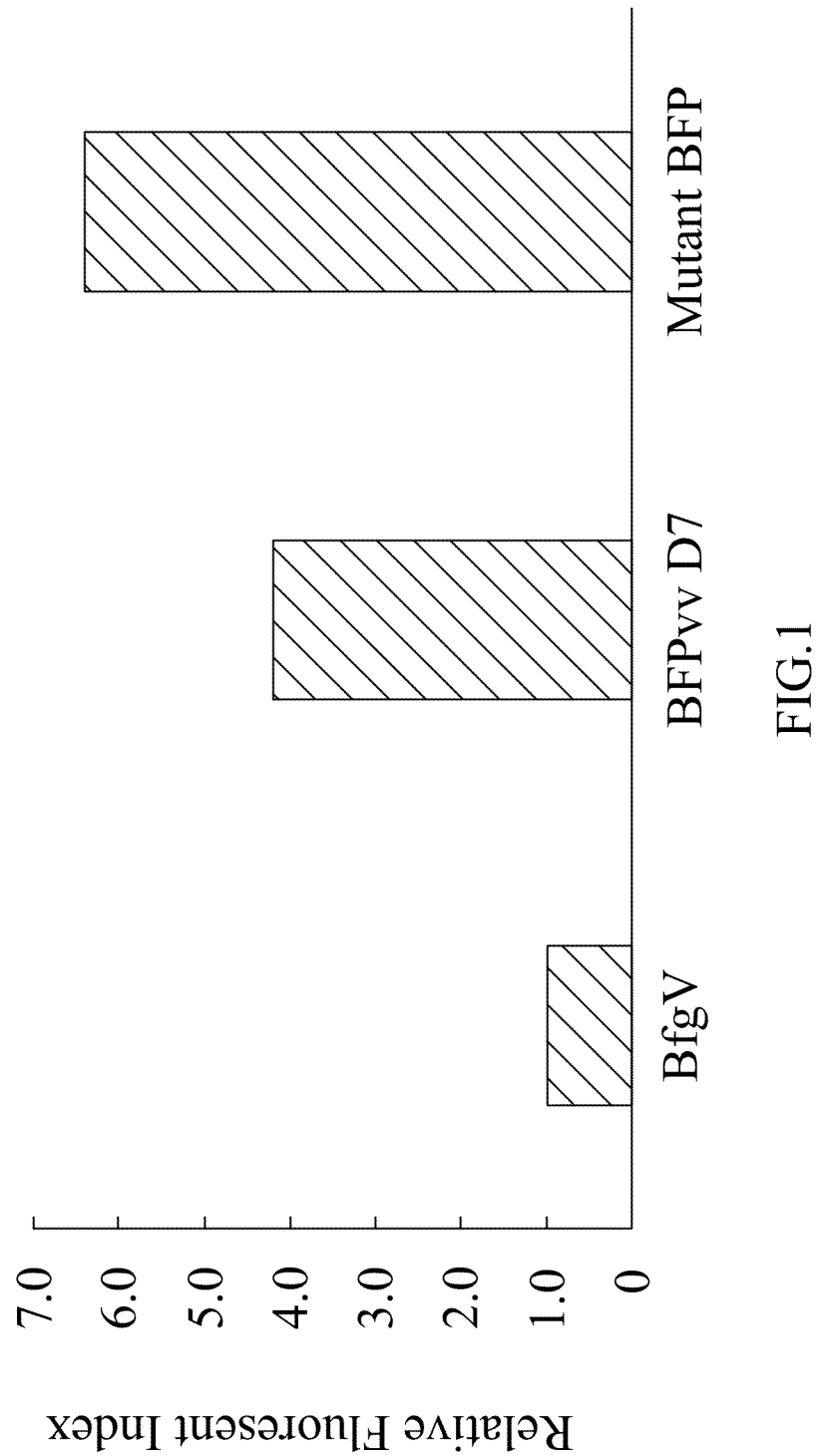
FIG. 1 illustrates a histogram of relative fluorescent intensities of BfgV and BFPvv D7 in the prior art and the mutant BFP in accordance with a preferred embodiment of the present invention.

The term "mutant blue fluorescent protein (BFP)" as used herein refers to the upgrade from the BFPvv D7 of SEQ ID NO:2 derived from the wild type BFP, BfgV of SEQ ID NO:1, obtained from *Vibrio vulnificus*.

Construction of Mutant BFP

The present invention provides a mutant blue fluorescent protein (BFP) that can be mutated by an error-prone PCR method or a DNA shuffling method with using the BFPvv D7 of SEQ ID NO:2 as parents as described as follows:

Bacterial Strains and Growth Medium: *E. coli* BL21(DE3) (Stratagene; CA, USA) was used as a host for gene expression and screening work. Bacteria used in the present invention were raised in Luria-Bertani (LB) broth or on LB agar. When required, 100 μg/ml ampicillin was added into the medium. Isopropylthio-b-D-galactoside (IPTG) was used as inducer at 1 mM in broth and 0.1 mM in agar plates. All medium components were purchased from Difco (MI, USA) and chemicals were from Sigma (MO, USA).

Plasmid Construction: A 751-bp fragment containing a complete 720-bp open reading frame (ORF) of BFPvv D7 of SEQ ID NO:2 and 31-bp upstream noncoding sequence was inserted into pET21b vector (Novagen; WI, USA). This recombinant plasmid was called pFP21. The BFPvv D7 in pFP21 replaced by its evolved mutant BFP was designated as pmBFP21. The plasmid pGFP (Clontech; CA. USA) containing wild type GFP gene which can express in *E. coli* was used to compare with pmBFP21 for fluorescent formation. The p19mBFP plasmid was identical to pGFP except that GFP was replaced by mBFP.

Random Mutagenesis: Random mutation was performed on entire bfgV gene by error-prone PCR. A 100 μl reaction mixture contained 50 mM Tris (pH 8.3), 6.6 mM $MgCl_2$, 50 mM KCl, 0.5 mM $MnCl_2$, 200 μM dNTP mixture, 50 μmol each of oligonucleotide primer, 20 ng template DNA, and 3 U Taq DNA polymerase (Promega; WI, USA). Two primers, EP-F1 (50-CTA CGC ATC TAG AAG CCA AAA CGG C-30) and EP-R1 (50-GTG ATA AGC TCG AGC GGT TAT GG-30), were designed for PCR. Thermal cycling was performed with the following conditions: 1 cycle of 94° C. for 30 s; 30 cycles of 94° C. for 10 s, 60° C. for 15 s, and 72° C. for 40 s, followed by 1 cycle of 72° C. for 10 min. The PCR products were purified by QIAquick Gel Extraction Kit (QIAGEN; Hilden, Germany) and inserted into pET21b. These recombinant plasmids were then transferred into BL21 (DE3) to become a mutant BFP library.

DNA Shuffling: All 751-bp inserts in candidate plasmids were amplified by normal PCR. An equal amount of each PCR product was mixed. About 400 ng of this mixture was dissolved into 18 μl of 10 mM Tris buffer (pH 7.5) and then 2 μl of 10× DNase I digestion buffer (500 mM Tris-HCl, pH 7.5, 10 mM $MnCl_2$) was added. This DNA mixture was digested by DNase I (Sigma) for 15-30 min. DNA fragments around 50 bp were purified from 2% agarose gel and then resuspended in 50 μl PCR mixture (10 mM Tris-HCl, pH 9.0, 0.2 mM dNTP, 1.5 mM $MgCl_2$, 50 mM KCl, 0.1% Triton X-100, and 1.5 U Taq DNA polymerase). Primerless PCR was then carried out with the following conditions: 1 cycle of 94° C. for 40 s; 35 cycles of 94° C. for 20 s, 50° C. for 10 s, and 72° C. for 10 s, followed by 1 cycle of 72° C. for 5 min. After adequate dilution of this PCR product, 40 additional PCR cycles were performed under the existence of EP-F1 and EP-R1 primers. These reassembled fragments were cloned back into pET21b for screening.

Mutant Screen: Transformed BL21(DE3) cells were raised on LBAI agar (LB agar containing 50 μg/ml ampicillin and 0.1 mM IPTG) at 37° C. for 16 h and then illuminated with long wavelength ultraviolet equipped in an ImageMaster VDS system (Amersham-Pharmacia; NT, HK). Colonies with fluorescence brighter than the one selected from previous round were picked out for further confirmation. All selected candidates were subjected to broth culture for fluorescent index (FI) determination. In brief, each transformant was first inoculated into 20 ml LBA broth and cultured at 37° C. for 16 h with 200 rpm shaking. Then, 0.5 ml of this overnight culture was inoculated into 50 ml LB broth for 1.5 h cultivation. IPTG was added to induce protein synthesis and then broth was incubated for another 1.5 h. At last, cells were collected and washed three times with ice-cold 50 mM phosphate buffer (pH 7.5). Two milliliters of each well-diluted cell suspension was subjected to fluorescence determination in a Perkin-Elmer LS50B luminescence spectrometer with the excitation wavelength at 352 nm and emission wavelength at 440 nm. Fluorescent intensity normalized by OD 600 of each sample was designed as fluorescent index (FI).

Determination of Fluorescent Spectra: Transformed *E. coli* cells were raised and collected as the same way in mutant screen except the addition of IPTG at the beginning of 50 ml culture. The way of determining the fluorescent spectra of *E. coli* transformants was the same as the previous report of the present inventor (Chang et al., 2004 (vol. 319)).

Please refer to FIG. 1 for a histogram of relative fluorescent intensities of BfgV and BFPvv D7 in the prior art and the mutant BFP in accordance with a preferred embodiment of the present invention. In the figure, the mutant BFP having the amino acid sequence of SEQ ID NO:3 according to the present invention has larger fluorescent intensity than a BFPvv D7 of SEQ ID NO:2 derived from a wild type BFP, BfgV of SEQ ID NO:1, obtained from *Vibrio vulnificus*.

Protein Synthesis and Fluorescent Formation of Mutant BFP

Figure 2:
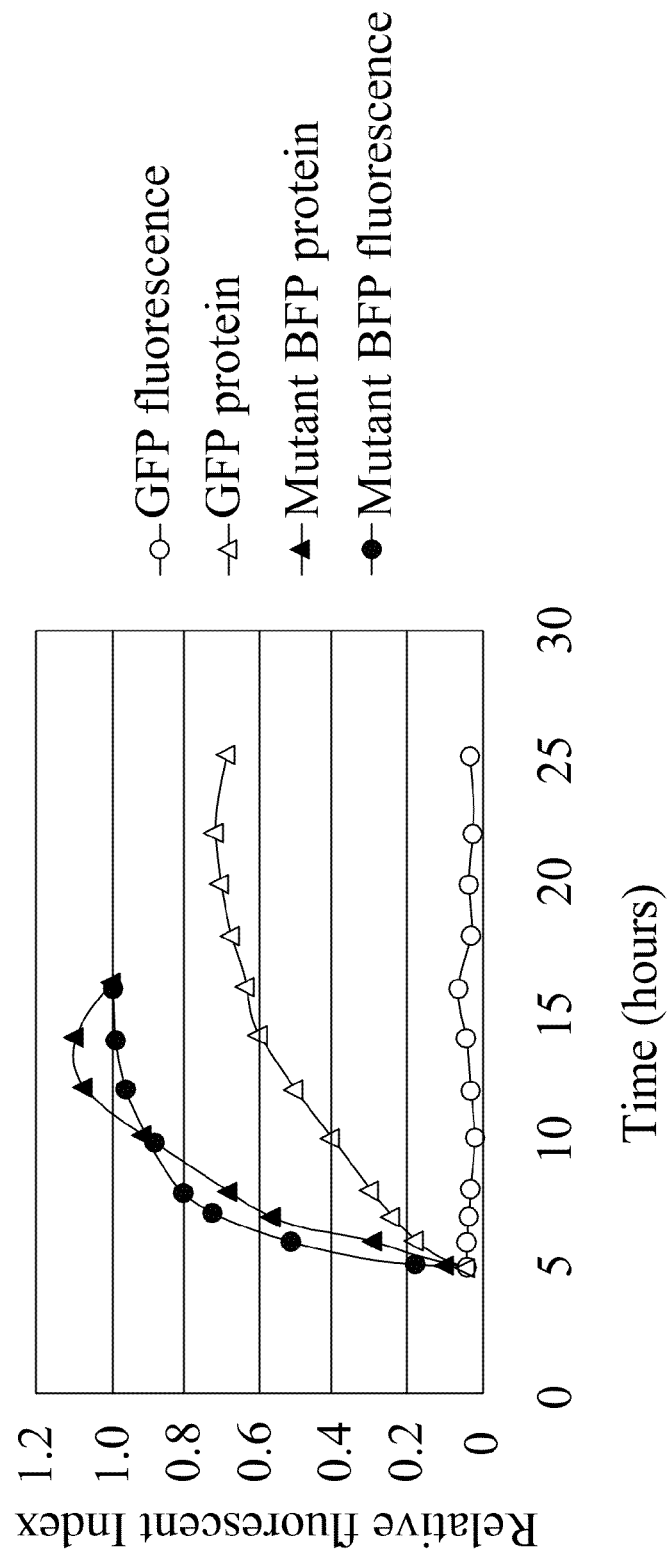
FIG. 2 illustrates a kinetic curve of protein synthesis and fluorescence formation of the mutant BFP having the amino acid sequence of SEQ ID NO:3 in accordance with a preferred embodiment of the present invention and a wild type GFP in the prior art in vivo.

Fluorescence of GFP relies on a specific fluorophore and the formation of this structure is oxygen-dependent. However, the fluorescence of the mutant BFP according to the present invention comes from NADPH binding. To clarify if there was any difference between protein synthesis and fluorescent formation in vivo, BL21(DE3)/pmBFP21 and BL21(DE3)/pGFP transformants were cultured and then analyzed. BL21(DE3)/pmBFP21 or BL21(DE3)/pGFP transformants were grown at 37° C. in LBA broth with 200 rpm shaking. Samples were taken at specific time points. An equal amount of cells taken from each sample was applied to SDS-PAGE for protein analysis. Relative FI of each sample was also determined. The excitation and emission wavelengths were respectively 352 nm and 440 nm for the mutant BFP, and respectively 395 nm and 509 nm for GFP. As shown in FIG. 2, time course analysis clearly showed the fluorescence of wild type GFP significantly fell behind GFP synthesis, but the protein synthesis and fluorescence appearance of the mutant BFP having the amino acid sequence of SEQ ID NO:3 comprises S176R and V178I mutations according to the present invention looked synchronic. The "synchronic" property of the mutant BFP suggested NADPH bound to this protein as soon as it was synthesized in cells.

Fluorescence of Mutant BFP in Anaerobic System

Figure 3:
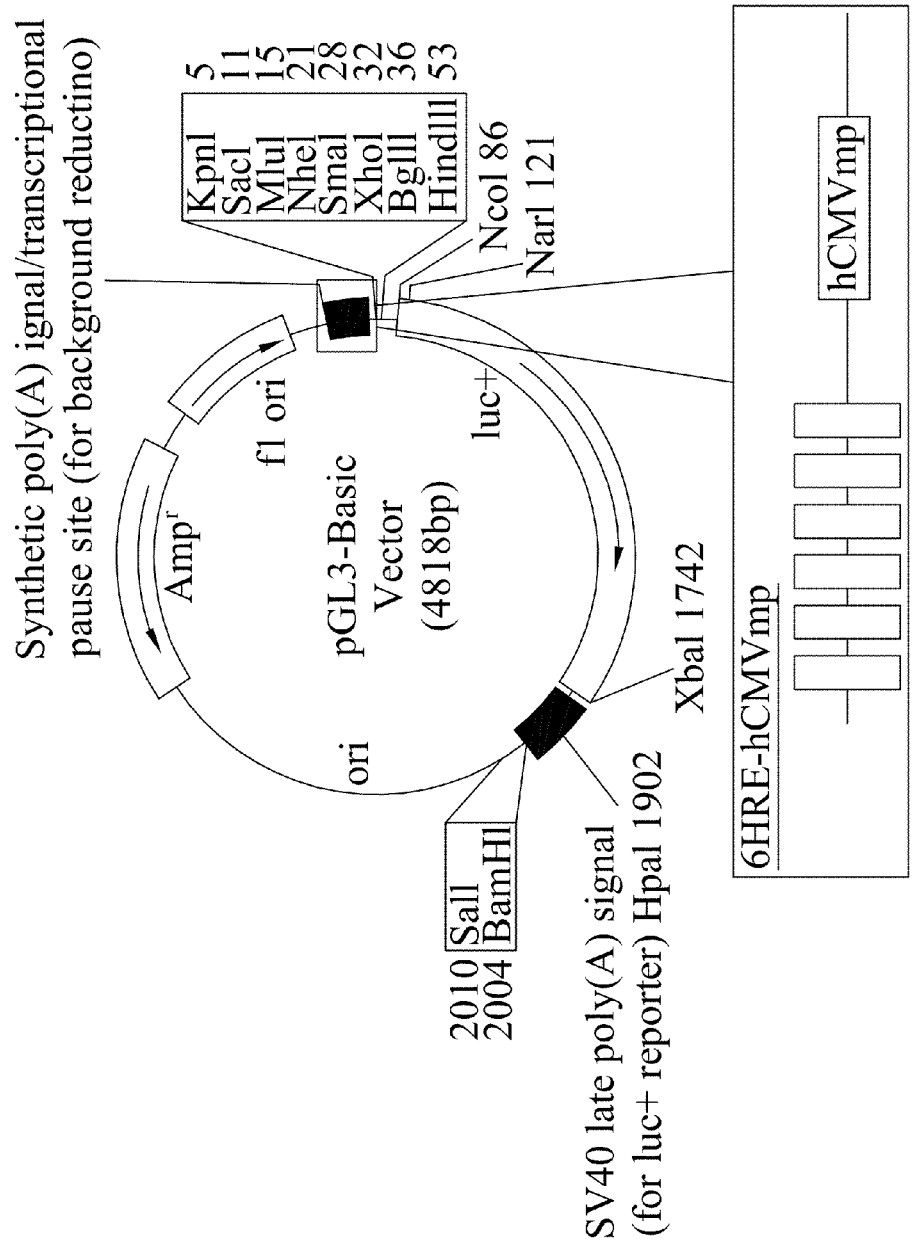
FIG. 3 illustrates a schematic diagram of a pGL3-basic vector inserted with a hypoxia response element (6HRE)-hCMVmp gene fragment in accordance with a preferred embodiment of the present invention.
Figure 4:
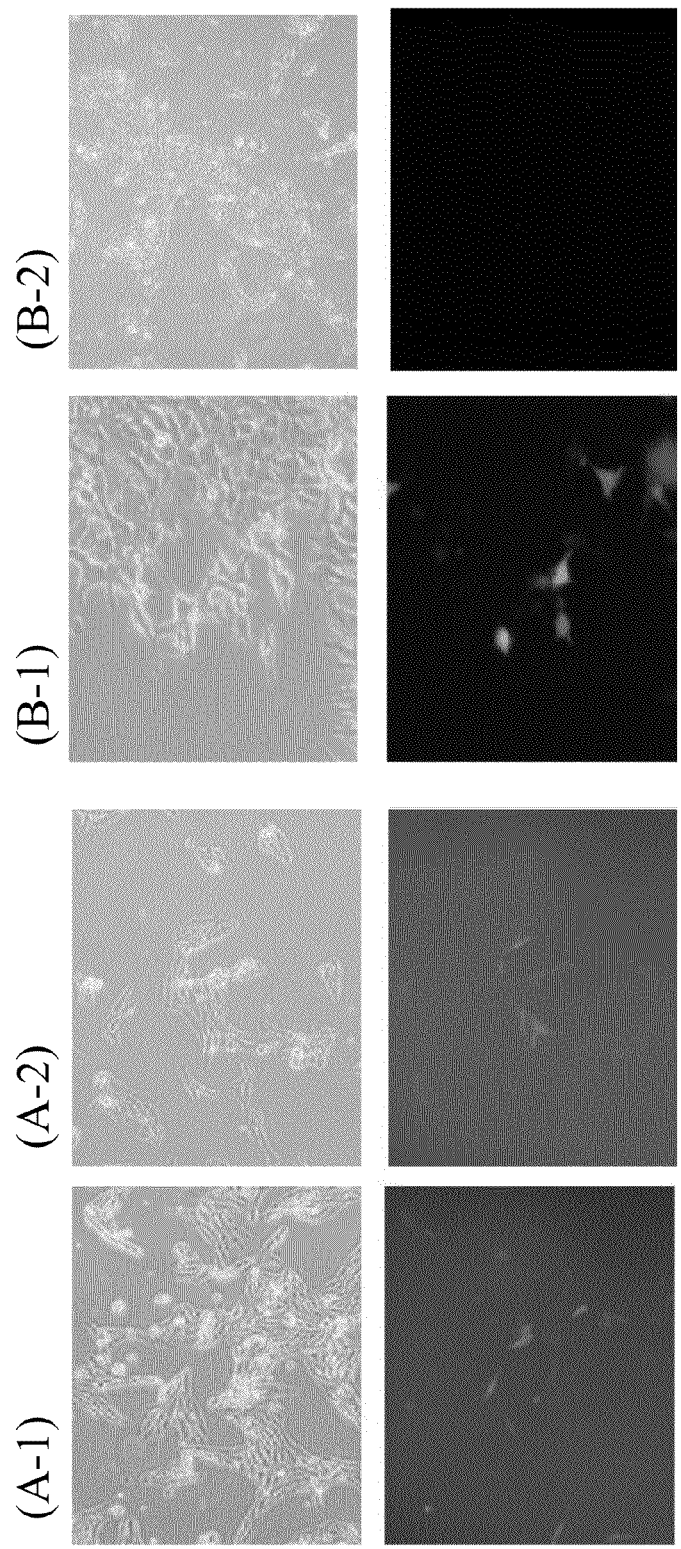
FIGS. 4(A) and 4(B) illustrate fluorescent expression images of the mutant BFP having the amino acid sequence of SEQ ID NO:3 in accordance with a preferred embodiment of the present invention and a wild type GFP in the prior art under normaxia and hypoxia, respectively.

Please refer to FIG. 3 for a schematic diagram of a pGL3-basic vector inserted with a hypoxia response element (6HRE)-hCMVmp gene fragment according to the present invention. Therefore, the mutant protein according to the present invention inserted into pGL3-basic vector can be expressed in the HeLa cells under hypoxia. As shown in FIG. 4 in which the HeLa cells with the mutant protein according to the present invention are cultured under normaxia (FIG. 4A-1) and hypoxia (FIG. 4A-2), respectively, and the HeLa cells with the wild type GFP in the prior art are cultured under normaxia (FIG. 4B-1) and hypoxia (FIG. 4B-2), respectively. In the FIG. 4, it can be found that the mutant protein according to the present invention can fluoresce with a blue light under both normaxia (FIG. 4A-1) and hypoxia (FIG. 4A-2). However, the wild type GFP in the prior art only fluoresces under normaxia (FIG. 4B-1) with a green light, but not under hypoxia (FIG. 4B-2).

Fluorescent Expression of Mutant BFP in Prokaryotic Cell and Eukaryotic Cell

Figure 5:
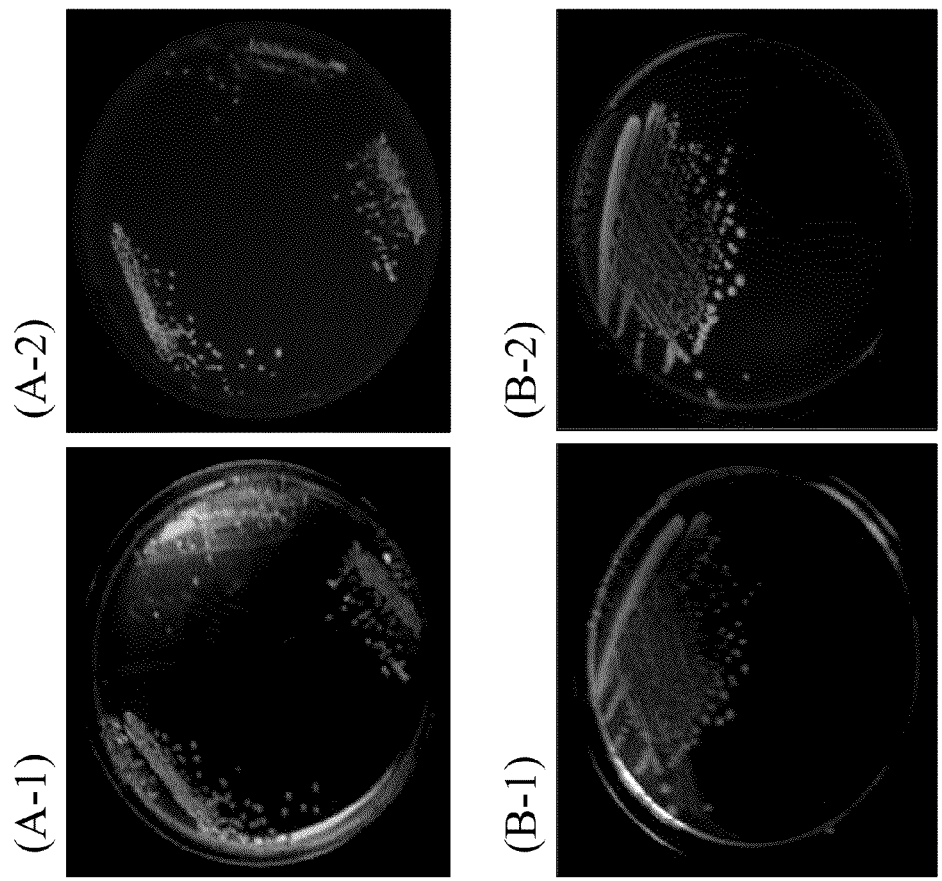
FIGS. 5(A) and 5(B) illustrate fluorescent expression images of the mutant BFP having the amino acid sequence of SEQ ID NO:3 in *E. coli* cells and *Vibrio vulnificus* cells, respectively, in accordance with a preferred embodiment of the present invention.
Figure 6:
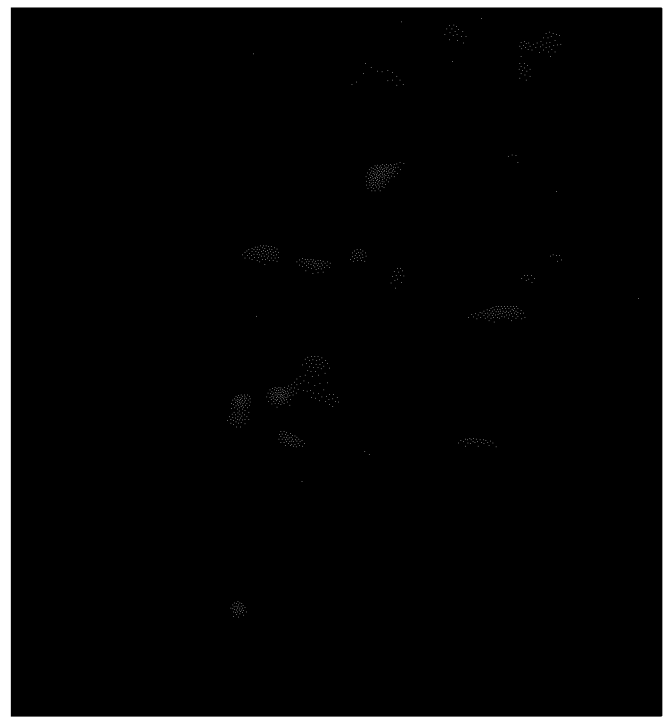
FIG. 6 illustrates fluorescent expression images of the mutant BFP having the amino acid sequence of SEQ ID NO:3 in HEK293T cells in accordance with a preferred embodiment of the present invention.
Figure 6:
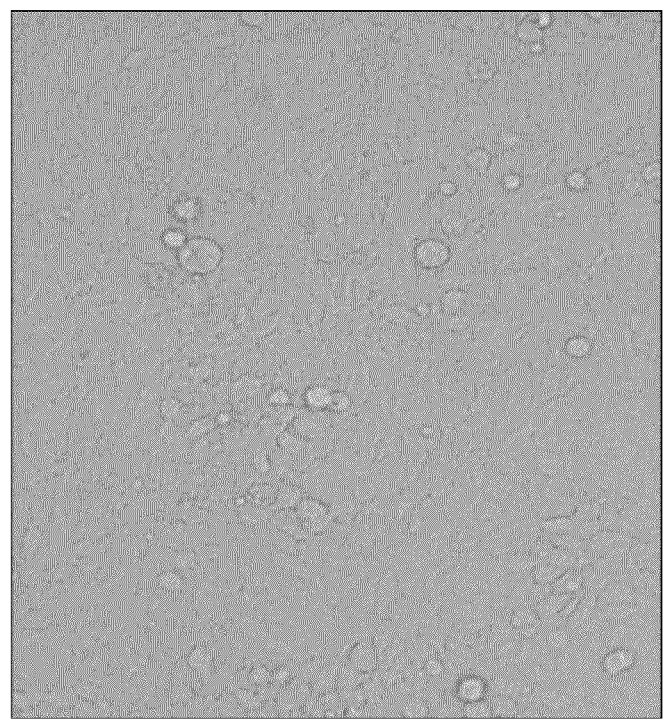

The mutant BFP of the present invention can be encoded, expressed, and purified by any one of a number of recombinant technology methods known to those skilled in the art, thereby not described in detail herein. The preferred production method will vary depending upon many factors and considerations, including the cost and availability of materials and other economic considerations. The optimum production procedure for a given situation will be apparent to those skilled in the art through minimal experimentation. A nucleic acid comprising a sequence encoding the mutant BFP of the present invention can be introduced into a variety of host cells comprising prokaryotic cells and eukaryotic cells, such as bacterial cells, yeast cells, fungal cells, insect cells, plant cells or animal cells. The methods by which the exogenous genetic material is introduced into such host cells are well known in the art. The sequences coding for the mutant BFP of the present invention are provided and such sequences may include the incorporation of codons "preferred" for expression by selected host strains, the provision of sites of cleavage by restriction endonuclease enzymes, and/or the provision of additional initial, terminal, or intermediate DNA sequences which facilitate construction of readily expressed vectors. As shown in FIGS. 5 and 6, it can be found that the mutant BFP of the present invention can fluoresce no matter in prokaryotic cells comprising in *E. coli* cells (without UV-excitation in FIG. 5A-1 and with UV-excitation in FIG. 5A-2) and *Vibrio vulnificus* cells (without UV-excitation in FIG. 5B-1 and with UV-excitation in FIG. 5B-2), or eukaryotic cells comprising HEK293T cells (without UV-excitation in FIG. 6A and with UV-excitation in FIG. 6B).

BFPs for FRET

Figure 7:
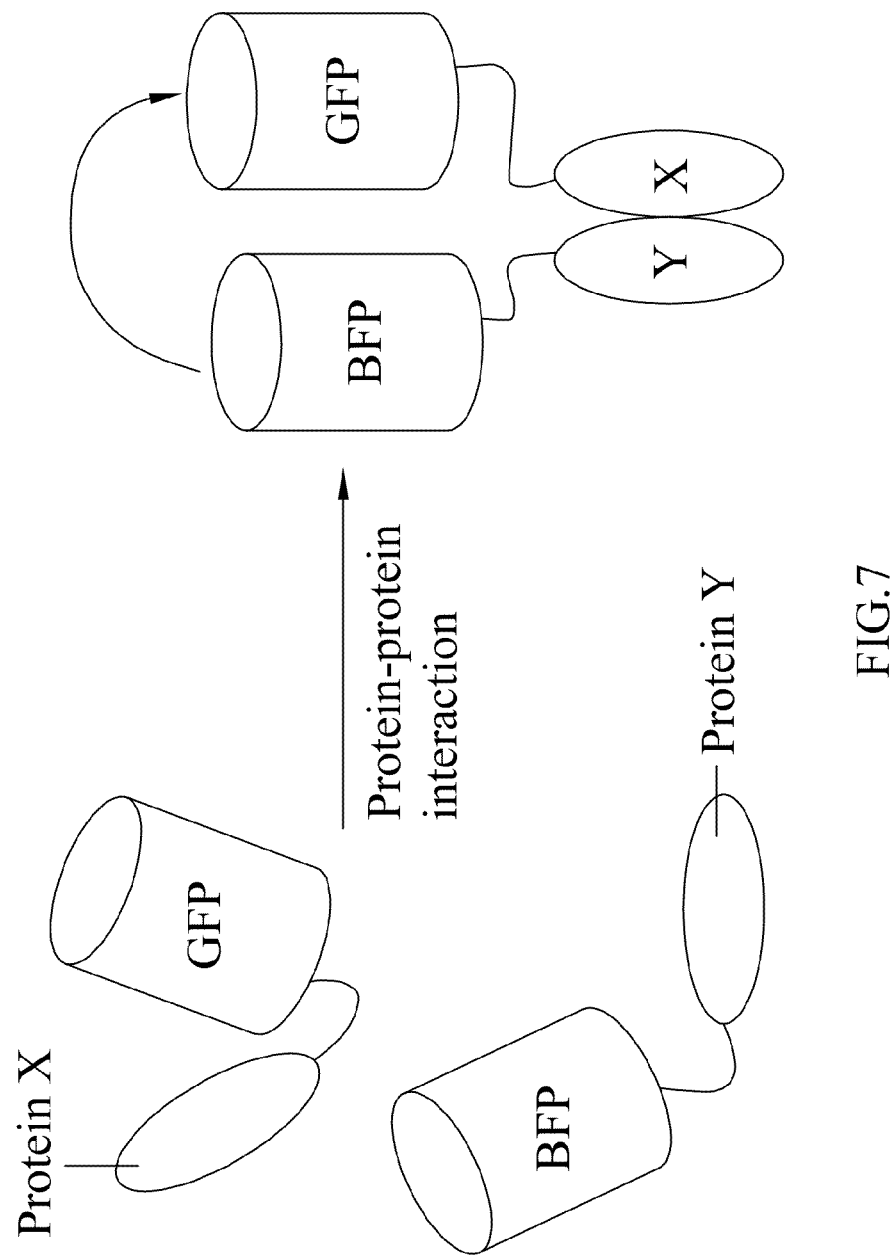
FIG. 7 illustrates a schematic diagram of a FRET method in which one of BFPs from *Vibrio vulnificus* is used as a donor fluorophore and coupled with one of several green fluorescent protein (GFP) variants as an acceptor fluorophore.

Besides, blue fluorescent proteins (BFPs) comprising the mutant BFP of the present invention, the BFPvv D7 of SEQ ID NO:2, or the BfgV of SEQ ID NO:1 are found with massive potential of diverse biotechnological and biomedical applications, such as fluorescence resonance energy transfer (FRET). Fluorescent proteins that display FRET can have rendered created a powerful impact for they enable measurement of molecular-scale distances with fluorescence changes. In fact, FRET-based approaches have allowed, if otherwise, intractable measurements of molecular concentrations, and they will bind interactions and catalytic activity. As further observed, it is confirmed that the BFPs from *Vibrio vulnificus* can fruitfully successfully behave as a FRET donor with GFP, as shown in FIG. 7 for a schematic diagram of a FRET method, wherein one of BFPs from *Vibrio vulnificus* bound with protein-Y is used as a donor fluorophore and coupled with one of several green fluorescent protein (GFP) variants bound with protein-X as an acceptor fluorophore.

In a preferred embodiment of the present invention, a method of using a BFP for FRET comprises using the mutant BFP of SEQ ID NO:3 as a donor fluorophore, and an enhanced GFP (EGFP) as an acceptor fluorophore. The FRET method is known to those skilled in the art, hence just described simply herein. In this embodiment, a pBAD/HisB vector is used as an expression vector. Firstly, the mutant BFP gene is cloned into pBAD/HisB vector using the restriction endonuclease enzyme XhoI/BglII, and the EGFP then is cloned into pBAD/HisB vector by the restriction endonuclease enzyme EcoRI/HindIII so as to form an expression vector, pBAD/HisB-mutant BFP-EGFP. This expression vector is sent into *E. coli* to express overnight, and then the obtained liquid after expression is excited at 352 nm of the excitation wavelength of the mutant BFP.

Figure 8:
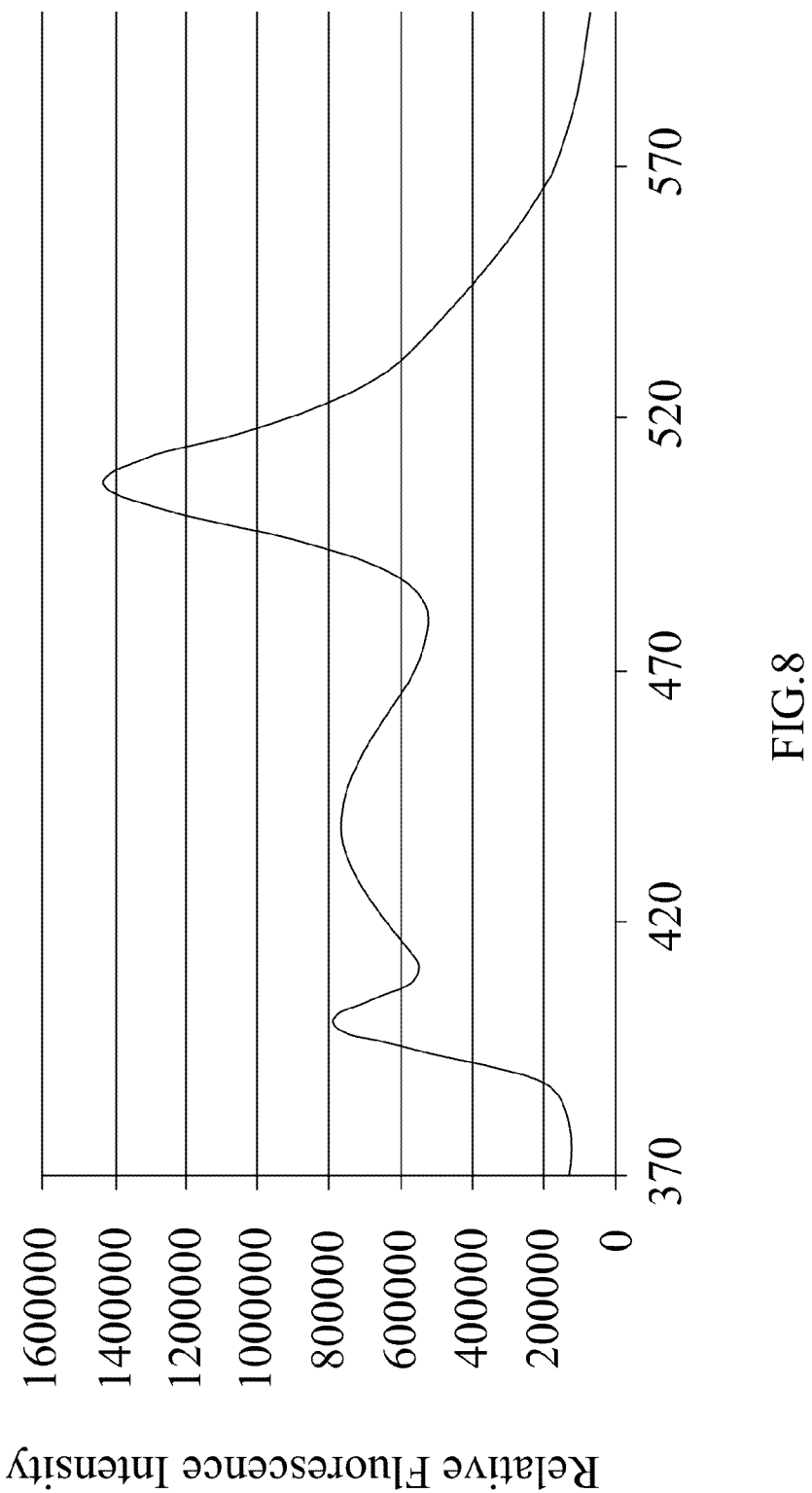
FIG. 8 illustrates a curve of relative fluorescence intensity versus wavelength in an aerobic FRET (mutant BFP coupled with EGFP) at 352 nm excitation in accordance with a preferred embodiment of the present invention.
Figure 9:
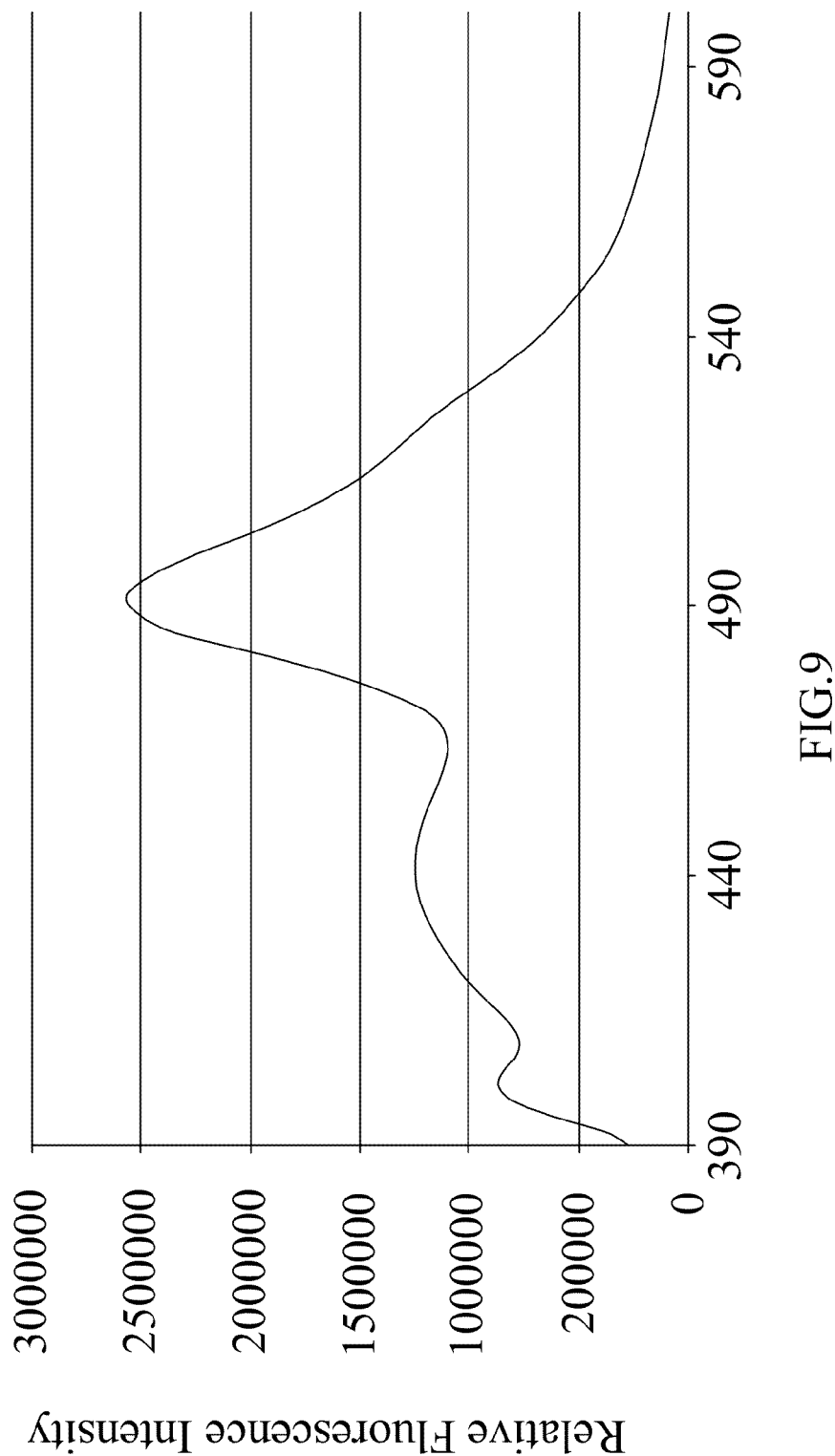
FIG. 9 illustrates a curve of relative fluorescence intensity versus wavelength in an anaerobic FRET (mutant BFP coupled with EGFP), respectively, at 352 nm excitation in accordance with a preferred embodiment of the present invention.
Figure 10:
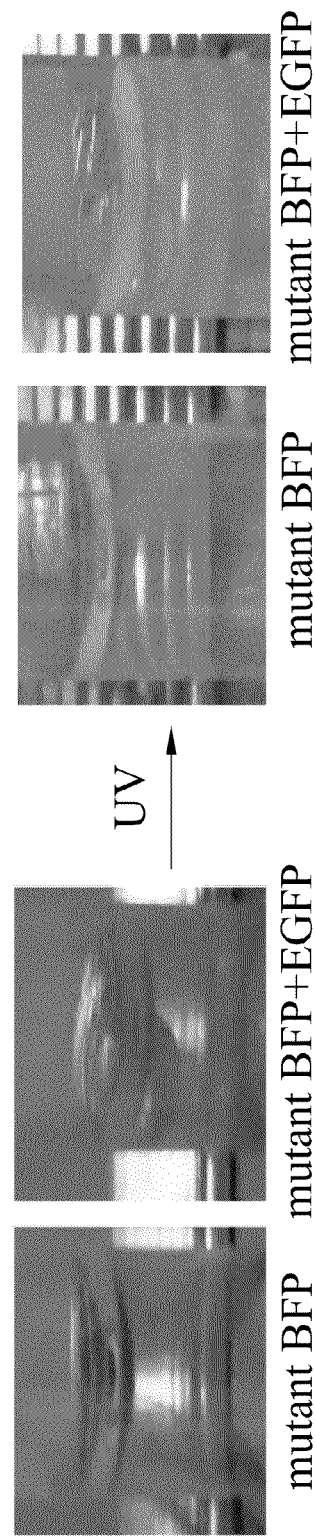
FIG. 10 illustrates fluorescent expression images of the mutant BFP coupled with EGFP at UV-excitation in accordance with a preferred embodiment of the present invention.

Please refer to FIGS. 8 and 9 for curves of relative fluorescence intensities versus wavelengths in an aerobic FRET (mutant BFP coupled with EGFP) and an anaerobic FRET (mutant BFP coupled with EGFP), respectively, at 352 nm excitation. They can be found that no matter where the system is aerobic or anaerobic, there exists a 509 nm peak that is the emission wavelength of the EGFP when using the mutant BFP as donor. That is, the BFPs from *Vibrio vulnificus* can indeed be applied for FRET well. As shown in FIG. 10, it can be found the mutant BFP coupled with EGFP can emit a green light when using UV-excitation. Nonetheless, if a FRET works as donor, BFPvv should display, to the moment, the shortest excitation and emission wavelength of all fluorescence proteins, providing a new option in single FERT pair or a design in multiple FRET experiment. Besides, the method of using the BFP for FRE in accordance with the present invention is also suitable for use in detecting a $Ca^{2+}$ concentration or caspase-3 activation in an apoptotic cell.

BFPs for Blue Fluorescent Fish

Figure 11:
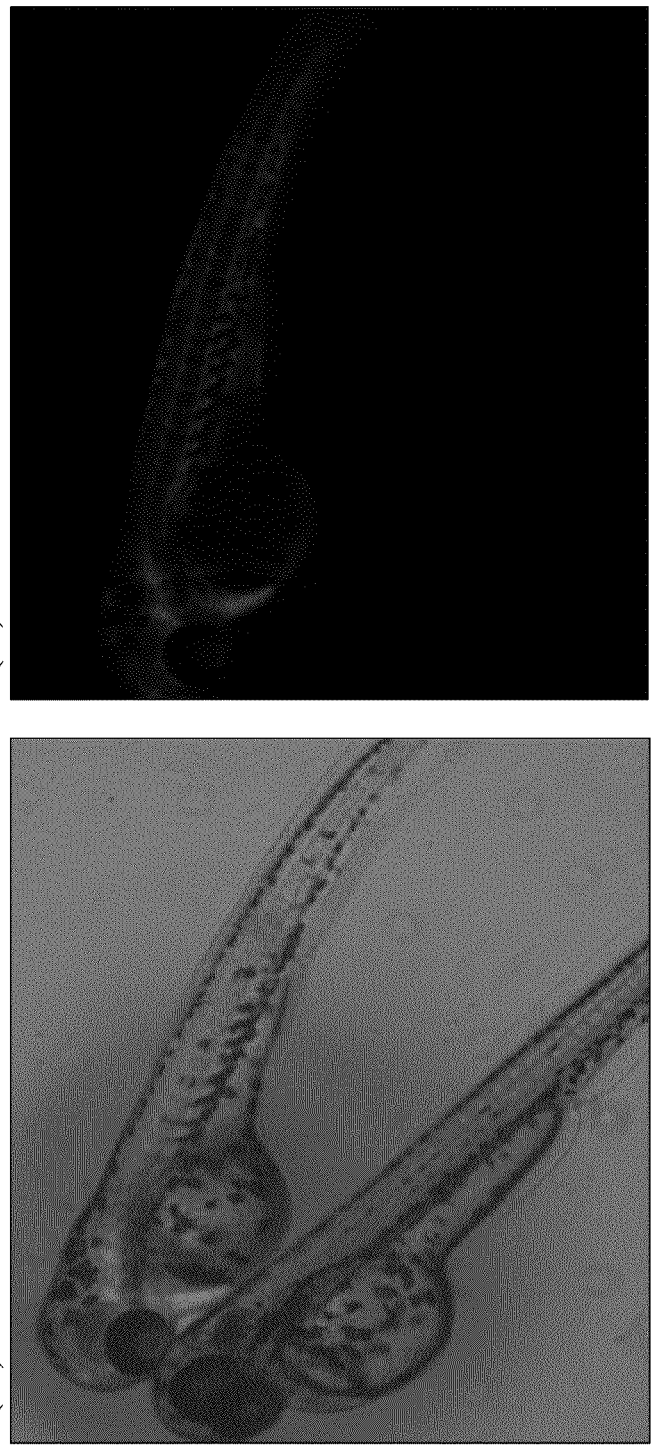
FIG. 11 illustrates fluorescent expression images of a *Danio rerio* blue fluorescent fish in accordance with a preferred embodiment of the present invention.

At present, there has existed green fluorescent fishes and red fluorescent fishes on the market, but still not having blue fluorescent fishes due to blue fluorescent protein with a undesirably low fluorescence quantum yield (QY) and easy to photobleaching. However, according to the present invention, the BFPs from *Vibrio vulnificus* with high fluorescence quantum yield and not easy to photobleaching can successfully be applied for producing a blue fluorescent fish. The method for producing a blue fluorescent fish is known to those skilled in the art, hence just described in brief herein. In this embodiment of the present invention, a linearized BFP DNA comprising the mutant BFP, the BFPvv D7 of SEQ ID NO:2, or the BfgV of SEQ ID NO:1 is injected into the cytoplasm of a *Danio rerio* zygote and the linearized BFP DNA is activated by a beta-actin promoter. The obtained blue fluorescent fish is as shown in FIG. 11.

As recapitulation, it is our belief that mutant BFP series can offer researchers with an even more powerful tool to the investigation of in life science research.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

---

What is claimed is:

1. An isolated mutant blue fluorescent protein (BFP), having the amino acid sequence set forth in SEQ ID NO: 3.

2. The isolated mutant BFP as claimed in claim 1, the fluorescent intensity of which is stable at 37° C.

3. The isolated mutant BFP as claimed in claim 1, having a propensity to form a monomer.

4. The isolated mutant BFP as claimed in claim 1, fluorescing through binding to NADPH with no need of undergoing a maturation step before emitting fluorescence.

5. The isolated mutant BFP as claimed in claim 1, having fluorescence spectra with an excitation peak at 352 nm and an emission peak at 440 nm.

6. The isolated mutant BFP as claimed in claim 1, which is 1.2-4 times the fluorescent intensity of Blue Fluorescent Protein from *Vibrio vulnificus* (BFPvv D7) set forth in SEQ ID NO:2.

* * * * *